(12) United States Patent
Miyamoto et al.

(10) Patent No.: US 9,616,249 B2
(45) Date of Patent: Apr. 11, 2017

(54) RADIOTHERAPY CONTROL APPARATUS AND RADIOTHERAPY CONTROL PROGRAM

(71) Applicant: NATIONAL UNIVERSITY CORPORATION HOKKAIDO UNIVERSITY, Sapporo-shi, Hokkaido (JP)

(72) Inventors: Naoki Miyamoto, Sapporo (JP); Shinichi Shimizu, Sapporo (JP); Taeko Matsuura, Sapporo (JP); Chie Toramatsu, Sapporo (JP); Seishin Takao, Sapporo (KR); Hideaki Nihongi, Sapporo (JP); Yuichi Hirata, Sapporo (JP); Kikuo Umegaki, Sapporo (JP)

(73) Assignee: NATIONAL UNIVERSITY CORPORATION HOKKAIDO UNIVERSITY, Sapporo-Shi, Hokkaido (JP)

( * ) Notice: Subject to any disclaimer, the term of this patent is extended or adjusted under 35 U.S.C. 154(b) by 238 days.

(21) Appl. No.: 14/386,166

(22) PCT Filed: Feb. 26, 2013

(86) PCT No.: PCT/JP2013/054842
§ 371 (c)(1),
(2) Date: Oct. 3, 2014

(87) PCT Pub. No.: WO2013/140957
PCT Pub. Date: Sep. 26, 2013

(65) Prior Publication Data
US 2015/0087881 A1    Mar. 26, 2015

(30) Foreign Application Priority Data
Mar. 19, 2012    (JP) ................................. 2012-062215

(51) Int. Cl.
*A61N 5/10* (2006.01)
*A61B 6/00* (2006.01)
(Continued)

(52) U.S. Cl.
CPC ............ *A61N 5/1039* (2013.01); *A61B 6/022* (2013.01); *A61B 6/487* (2013.01); *A61B 6/5211* (2013.01);
(Continued)

(58) Field of Classification Search
CPC ................ A61N 5/1039; A61N 5/1037; A61N 2005/1061; A61N 2005/1074; A61B 6/487;
(Continued)

(56) References Cited

U.S. PATENT DOCUMENTS

2006/0093089 A1    5/2006  Vertatschitsch et al.
2008/0317203 A1*  12/2008  Ferrand ................ A61B 6/0457
                                                                378/65

FOREIGN PATENT DOCUMENTS

JP    2000167072 A    6/2000
JP    2006230673 A    9/2006
(Continued)

*Primary Examiner* — Courtney Thomas
(74) *Attorney, Agent, or Firm* — Muncy, Geissler, Olds & Lowe, P.C.

(57) ABSTRACT

A radiotherapy control apparatus includes a fluoroscopic image acquisition unit to acquire fluoroscopic images of markers in a patient from a single fluoroscopic imaging device, a projection line calculation unit to identify projected positions of the markers on the fluoroscopic image and calculate equations of projection lines linking these projected positions and a focus position of the imaging device, an inter-marker distance acquisition unit to acquire a distance between each pair of the markers, a marker position calculation unit to calculate current positions of the (Continued)

markers based on the equations and the distances, and a therapeutic radiation emission determination unit to determine whether to emit therapeutic radiation based on the current positions of the markers.

10 Claims, 8 Drawing Sheets

(51) Int. Cl.
 *A61B 6/02* (2006.01)
 *A61B 90/00* (2016.01)
(52) U.S. Cl.
 CPC ......... *A61N 5/1037* (2013.01); *A61N 5/1049* (2013.01); *A61B 2090/3966* (2016.02); *A61N 2005/1061* (2013.01); *A61N 2005/1074* (2013.01)
(58) Field of Classification Search
 CPC ............ A61B 19/54; A61B 2019/5466; A61B 6/5211; A61B 6/022
 See application file for complete search history.

(56) References Cited

FOREIGN PATENT DOCUMENTS

| | | | |
|---|---|---|---|
| JP | 2008507996 A | 3/2008 |
| JP | 2009502383 A | 1/2009 |

\* cited by examiner

RADIOTHERAPY CONTROL APPARATUS AND RADIOTHERAPY CONTROL PROGRAM

CROSS REFERENCE TO RELATED APPLICATIONS

This application is a national stage of International Application No.: PCT/JP2013/054842, which was filed on Feb. 26, 2013, and which claims priority to Japanese Patent Application No. 2012-062215 which was filed on Mar. 19, 2012, and which are both herein incorporated by reference.

TECHNICAL FIELD

The present invention relates to a radiotherapy control apparatus and radiotherapy control program used for radiotherapy, and more particularly, to a radiotherapy control apparatus and radiotherapy control program which can reduce a radiation exposure dose of a patient undergoing radiographic fluoroscopy.

BACKGROUND ART

Conventionally, in radiotherapy which administers treatment by irradiating an affected area of a patient with therapeutic radiation, it is important to position the therapeutic radiation with high precision and accurately measure the position of the affected area to be irradiated. This is because these operations allow a margin of a region irradiated with the therapeutic radiation to be reduced, thereby reducing a radiation exposure dose of normal tissue existing around the affected area.

However, when the affected area moves along with breathing, it is necessary to increase the margin of the irradiated region by taking the respiratory movements into consideration. To deal with this, breathing synchronized radiotherapy is used which irradiates an affected area of the patient with therapeutic radiation only in a particular breathing phase in order to reduce the margin of the irradiated region resulting from the respiratory movements and thereby reduce the radiation exposure dose of normal tissue. The breathing synchronized radiotherapy, which eliminates the need to give much consideration to the respiratory movements of an affected area, allows the margin of the irradiated region to be reduced.

In the breathing synchronized radiotherapy described above, markers are used to determine the breathing phase. Known examples of the markers include an in vitro marker which is kept track of via a pressure sensor pasted to body surface of the patient or an inhaled air sensor coupled to the mouth of the patient and an in vivo marker used to keep track of the marker inserted into the body, a bone structure, and diaphragmatic breathing exercise by continuous X-ray fluoroscopy (Patent Literatures 1 and 2).

CITATION LIST

Patent Literature

Patent Literature 1: Japanese Patent Laid-Open No. 2000-167072
Patent Literature 2: Japanese Patent Laid-Open No. 2006-230673

SUMMARY OF INVENTION

Technical Problem

However, conventional breathing synchronized radiotherapy using in vivo markers, including the inventions described in Patent Literatures 1 and 2, takes fluoroscopic images simultaneously along two directions using two X-ray fluoroscopes because it is necessary to measure three-dimensional position of the in vivo markers in real time during treatment. Consequently, there is a problem of increased risk that a large radiation exposure dose inflicted by radiographic radiation used for fluoroscopic observation during radiotherapy, coupled with a radiation exposure dose inflicted by therapeutic radiation, can cause radiation injuries.

The present invention has been made to solve the above problem and has an object to provide a radiotherapy control apparatus and radiotherapy control program capable of calculating the current positions of markers implanted in a patient by means of a single fluoroscopic imaging device and reducing a radiation exposure dose inflicted on the patient by radiographic radiation used for fluoroscopic observation during radiotherapy.

Solution to Problem

The present invention provides a radiotherapy control apparatus comprising: a fluoroscopic image acquisition unit adapted to acquire a fluoroscopic image of three or more markers implanted in the body of a patient from a single fluoroscopic imaging device adapted to take fluoroscopic images; a projection line calculation unit adapted to identify projected positions of the respective markers on the fluoroscopic image and calculate equations of respective projection lines linking together these projected positions and a focus position of the fluoroscopic imaging device; an inter-marker distance acquisition unit adapted to acquire each distance between each pair of the markers; a marker position calculation unit adapted to calculate current positions of the respective markers based on the equations of the projection lines and the inter-marker distances; and a therapeutic radiation emission determination unit adapted to determine whether to emit therapeutic radiation based on the current positions of the respective markers. The present invention also provides a radiotherapy control program configured to cause a computer to function as the components described above.

Also, in the present invention, when three-dimensional vectors $M_1$, $M_2$, and $M_3$ which represent the current positions of the respective markers are defined by Formula (1) below using three-dimensional direction vectors $a_1$, $a_2$, and $a_3$ of the respective projection lines and a three-dimensional vector b of the focus position, the marker position calculation unit may identify the three-dimensional vectors $M_1$, $M_2$, and $M_3$ by calculating $t_1$, $t_2$, and $t_3$ in Formula (1) below based on the three-dimensional vectors $a_1$, $a_2$, $a_3$, and b identified by the equations of the respective projection lines as well as on the inter-marker distances.

$$\vec{M}_1 = t_1 \vec{a}_1 + \vec{b}$$

$$\vec{M}_2 = t_2 \vec{a}_2 + \vec{b}$$

$$\vec{M}_3 = t_3 \vec{a}_3 + \vec{b} \qquad \text{Formula (1)}$$

Furthermore, the present invention further comprises: a first fluoroscopic image acquisition unit adapted to acquire a plurality of first fluoroscopic images taken by the single fluoroscopic imaging device along a first fluoroscopic direction; a second fluoroscopic image acquisition unit adapted to acquire a plurality of second fluoroscopic images taken by the single fluoroscopic imaging device along a second fluoroscopic direction different from the first fluoroscopic direction with second acquisition timing different from acquisition timing of the first fluoroscopic images; a first time-series data acquisition unit adapted to acquire time-sequential projected positions of the markers in the plurality of first fluoroscopic images as first time-series data; a second time-series data acquisition unit adapted to acquire time-sequential projected positions of the markers in the plurality of second fluoroscopic images as second time-series data; a correlation maximizing unit adapted to maximize a correlation between the first time-series data and the second time-series data by shifting a phase of the first time-series data or the second time-series data; and an estimated marker position calculation unit adapted to acquire equations of respective first projection lines linking the projected positions of the first time-series data with the focus position and equations of respective second projection lines linking the projected positions of the second time-series data with the focus position from the projection line calculation unit after the correlation is maximized by the correlation maximizing unit and calculate midpoints of respective common perpendicular lines to the first projection lines and the second projection lines as estimated positions of the markers, wherein the inter-marker distance acquisition unit may acquire the inter-marker distances based on estimated positions of the markers calculated by the estimated marker position calculation unit. Also, a computer may be caused to function as the components described above.

Also, in the present invention, the correlation maximizing unit may shift the phase of the first time-series data or the second time-series data so as to minimize length of the common perpendicular line to the first projection lines and the second projection lines.

Furthermore, the present invention may comprise a planned marker position acquisition unit adapted to acquire planned positions from a treatment planning data storage unit adapted to store data on treatment planning, the planned positions being three-dimensional positions of the markers at a time of the treatment planning, wherein the therapeutic radiation emission determination unit may compare the current position of each of the markers calculated by the marker position calculation unit with the planned position of the marker acquired by the planned marker position acquisition unit and thereby determine whether or not the current position falls within a predetermined tolerance of the planned position. Also, a computer may be caused to function as the components described above.

Advantageous Effects of Invention

Using a single fluoroscopic imaging device, the present invention can calculate the current positions of markers implanted in a patient and reduce a radiation exposure dose inflicted on the patient by radiographic radiation used for fluoroscopic observation during radiotherapy.

DESCRIPTION OF EMBODIMENTS

An embodiment of a radiotherapy control apparatus 1 and radiotherapy control program 1*a* according to the present invention will be described below with reference to the drawings. Note that the radiation as referred to herein is a concept which includes all of electromagnetic waves such as X-rays and gamma rays as well as particle beams such as a proton beam and heavy-particle beam.

Figure 1:
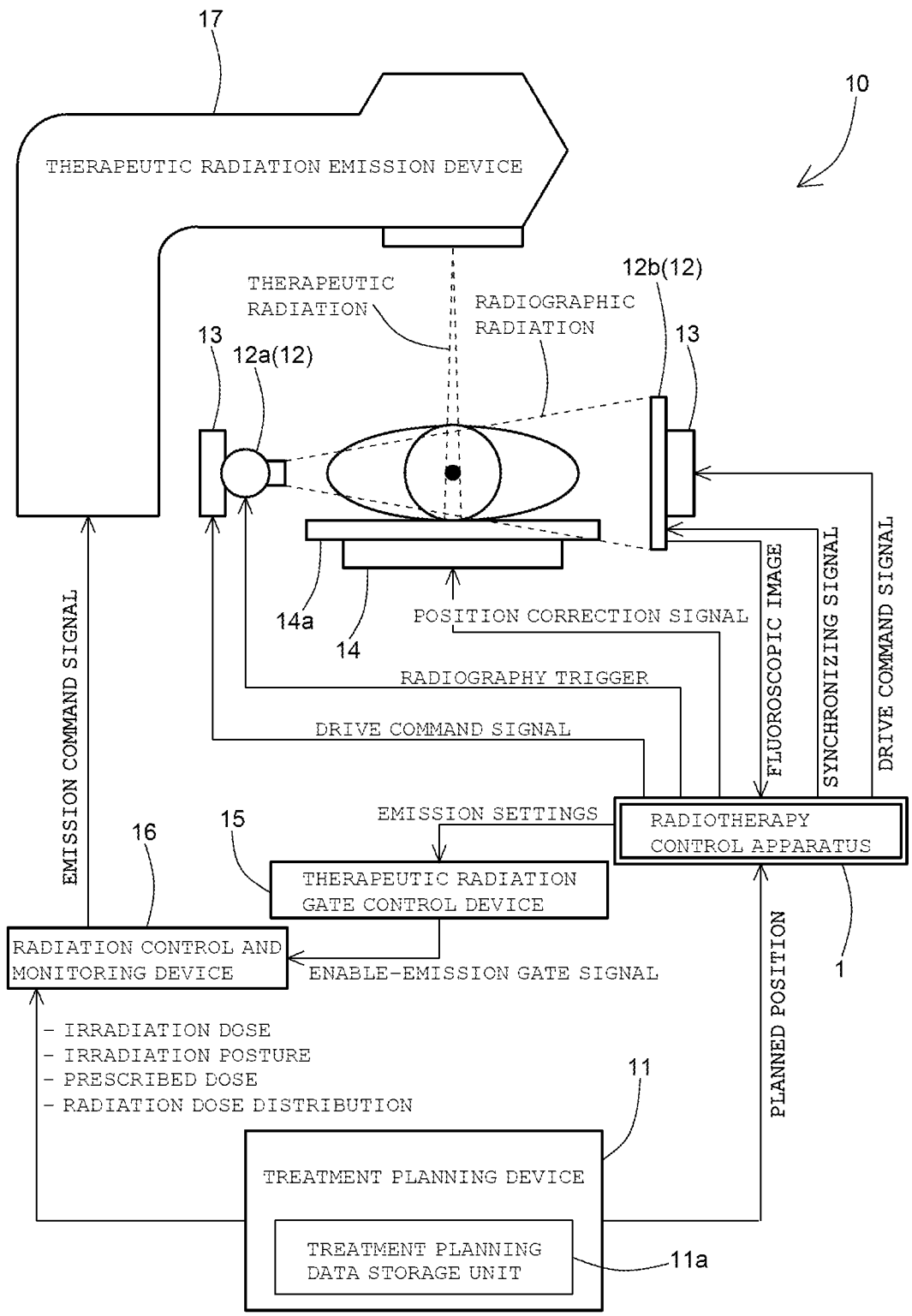
FIG. 1 is an overall configuration diagram showing a radiotherapy system including a radiotherapy control apparatus according to the present invention.

As shown in FIG. 1, a radiotherapy system 10 according to an embodiment of the present invention mainly includes a treatment planning device 11, a fluoroscopic imaging device 12, a fluoroscopic direction drive device 13, a patient bed drive device 14, a therapeutic radiation gate control device 15, a radiation control and monitoring device 16, and a therapeutic radiation emission device 17 as well as the radiotherapy control apparatus 1 according to the present embodiment. Individual devices will be described in detail below.

The treatment planning device 11 is used to create, in advance, a treatment plan for a patient who is to undergo radiotherapy. The treatment planning device 11 is made up of a personal computer and the like and is provided with a treatment planning data storage unit 11*a* adapted to store treatment planning data on treatment planning. According to the present embodiment, planned marker positions, which are three-dimensional positions of markers at the time of treatment planning, an irradiation sequence (irradiation doses, irradiation postures) at the planned marker positions, prescribed doses of therapeutic radiation to be given to the patient at the planned marker positions, a radiation dose distribution produced in the body of the patient as a result of irradiation with the therapeutic radiation, and the like are calculated and stored as the treatment planning data.

The planned marker positions described above are calculated based on CT (Computer Tomography) images of the patient taken during treatment planning before the start of the treatment and transmitted to the radiotherapy control apparatus 1. On the other hand, the irradiation sequence (irradiation doses, irradiation postures), prescribed doses, and irradiation dose distribution are transmitted to the radiation control and monitoring device 16.

Note that according to the present embodiment, in which breathing synchronized radiotherapy is conducted by emitting therapeutic radiation in a so-called expiratory phase (state after complete exhalation), CT images taken during treatment planning are obtained in the expiratory phase. However, the present invention is applicable not only to breathing synchronized radiotherapy in the expiratory phase, but also to breathing synchronized radiotherapy in any breathing phase. For example, when breathing synchronized radiotherapy is conducted in an inspiratory phase (state after complete inhalation), CT images taken in the inspiratory phase are used.

Note that a planned marker position may be established for only one of plural markers implanted in the body of the patient or for each of the plural markers. Also, a planned marker position may be set to a position (such as a center of gravity) uniquely defined out of plural markers. Furthermore, preferably the markers are made of a material, such as gold, platinum, or iridium, which causes relatively little harm to human bodies and absorbs radiation well, but are not limited to particular materials. Also, preferably the markers are cylindrical or spherical in shape, but other shapes are also available for use.

The fluoroscopic imaging device 12 is designed to take fluoroscopic images under radiographic radiation and is provided with a set of an X-ray generator 12a and an X-ray detector 12b. The X-ray generator 12a generates X-rays in response to a radiography trigger transmitted from the radiotherapy control apparatus 1. On the other hand, the X-ray detector 12b outputs a fluoroscopic image of the patient subjected to X-ray fluoroscopy to the radiotherapy control apparatus 1 in response to a synchronizing signal transmitted in synchronization with the radiography trigger. Note that, although X-rays are used as radiographic radiation in the present embodiment, other radiation may be used alternatively.

The fluoroscopic direction drive device 13 is intended to change a fluoroscopic direction of the fluoroscopic imaging device 12. Specifically, the fluoroscopic direction drive device 13 is installed on each of the X-ray generator 12a and X-ray detector 12b and designed to change a position and angle of the X-ray generator 12a and X-ray detector 12b in response to a drive command signal from the radiotherapy control apparatus 1, thereby switching between at least a first fluoroscopic direction and a second fluoroscopic direction different from the first fluoroscopic direction.

Note that according to the present embodiment, the fluoroscopic direction drive device 13 includes a stand movable along a floor, a ceiling, or a wall surface, and the like of a treatment room, and the X-ray generator 12a and X-ray detector 12b are fixed to the stand. Note that the configuration of fluoroscopic direction drive device 13 is not limited to the one described above, and the X-ray generator 12a and X-ray detector 12b may be attached to a movable fixture of a so-called C-arm type or mounted on a rotating gantry if the therapeutic radiation emission device 17 is equipped with the rotating gantry.

The patient bed drive device 14 is designed to drive the patient bed 14a on which the patient is placed and perform alignment when therapeutic radiation is emitted. Specifically, the patient bed drive device 14 is attached to the patient bed 14a and designed to change the position of the patient bed 14a in response to a position correction signal from the radiotherapy control apparatus 1 and thereby bring an estimated position of a marker described later into coincidence with a planned position during treatment planning.

The therapeutic radiation gate control device 15 is designed to control a gate signal which indicates whether to emit therapeutic radiation. According to the present embodiment, the therapeutic radiation gate control device 15 is configured to allow the radiotherapy control apparatus 1 to make emission settings for therapeutic radiation. Specifically, when the radiotherapy control apparatus 1 determines to emit radiation, an enable-emission gate signal turns on. On the other hand, when the radiotherapy control apparatus 1 determines not to emit radiation, the enable-emission gate signal turns off. Then, the therapeutic radiation gate control device 15 is designed to output the enable-emission gate signal to the radiation control and monitoring device 16.

The radiation control and monitoring device 16 are designed to control emission of therapeutic radiation from the therapeutic radiation emission device 17 and monitor a cumulative administered dose for the patient. According to the present embodiment, the radiation control and monitoring device 16 receives the irradiation sequence (irradiation doses, irradiation postures), prescribed doses, radiation dose distribution, and the like from the treatment planning device 11 and stores them. Then, if the enable-emission gate signal received from the therapeutic radiation gate control device 15 is on, the radiation control and monitoring device 16 outputs an emission command signal specified by the irradiation sequence to the therapeutic radiation emission device 17, giving an instruction to emit radiation.

Also, the radiation control and monitoring device 16 has a function to monitor a cumulative administered dose of therapeutic radiation during radiotherapy. Specifically, the radiation control and monitoring device 16 accumulates doses given to the patient and compares the cumulative administered dose as required with the prescribed dose acquired from the treatment planning device 11. Then, the radiation control and monitoring device 16 continues radiotherapy unless the cumulative administered dose reaches the prescribed dose, but notifies an operator that the radiotherapy or one of treatment procedures has finished when the cumulative administered dose reaches the prescribed dose.

Note that although in the present embodiment, therapeutic radiation gate control device 15 is interposed between the radiotherapy control apparatus 1 and radiation control and monitoring device 16, the present invention is not limited to this configuration. For example, if the radiation control and monitoring device 16 has functionality of the therapeutic radiation gate control device 15, there is no need to provide the therapeutic radiation gate control device 15 separately.

The therapeutic radiation emission device 17 is designed to irradiate an affected area of the patient with therapeutic radiation. Specifically, upon receiving an emission command signal from the radiation control and monitoring device 16, the therapeutic radiation emission device 17 irradiates the affected area of the patient with therapeutic radiation according to the irradiation sequence specified in the emission command signal. Note that although X-rays are used as therapeutic radiation in the present embodiment, other radiation may be used alternatively. Also, examples of the affected area of the patient include not only affected areas, such as cancers and malignant tumors, which require radiotherapy, but also other relevant treatment sites.

The radiotherapy control apparatus 1 is designed to control the radiotherapy conducted using the radiotherapy system 10 according to the present embodiment. According to the present embodiment, the radiotherapy control apparatus 1 measures three-dimensional positions of markers in real time based on fluoroscopic images taken along one direction by the single fluoroscopic imaging device 12. The radiotherapy control apparatus 1 according to the present embodiment will be described concretely below.

Figure 2:
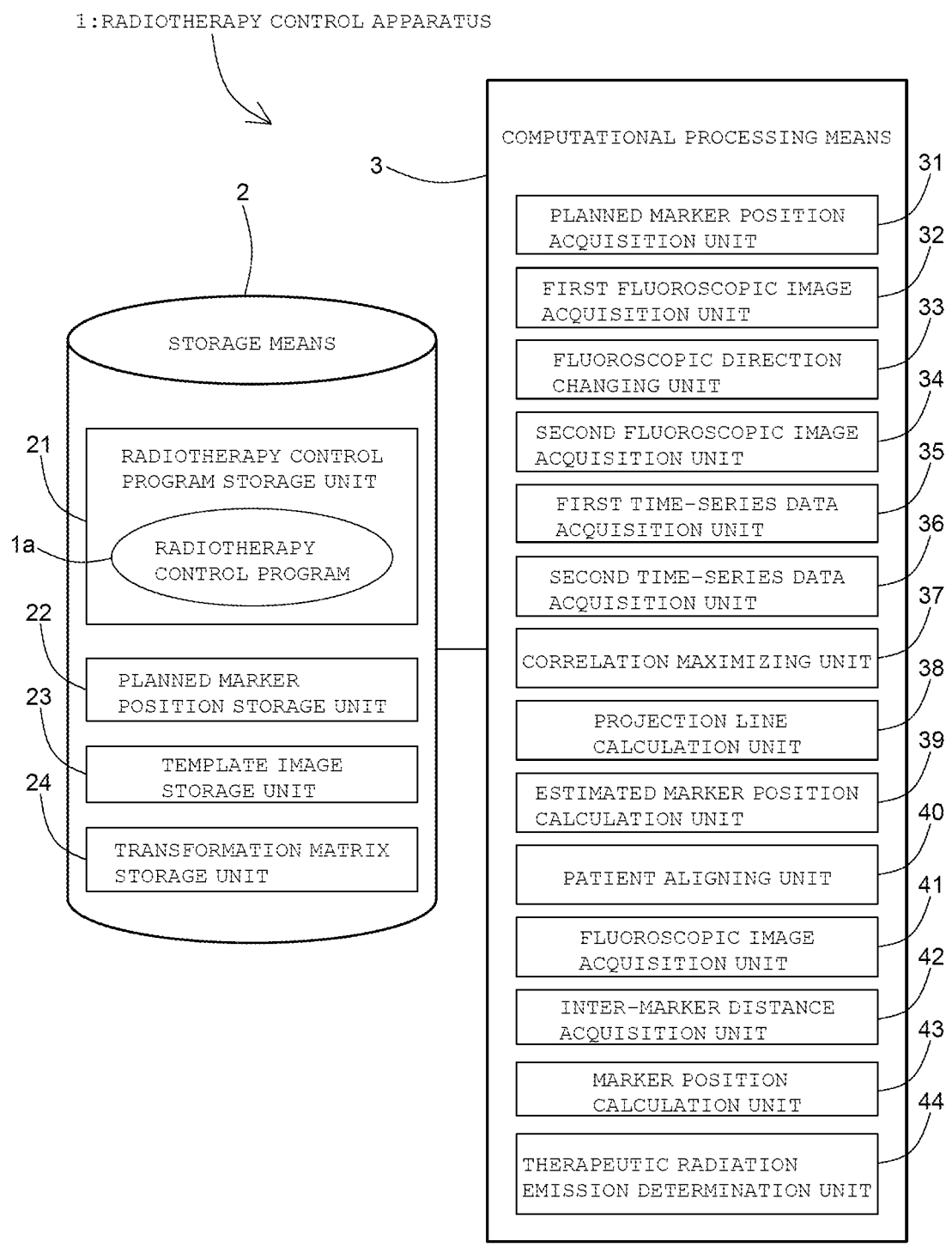
FIG. 2 is a block diagram showing a radiotherapy control apparatus according to an embodiment of the present invention.

The radiotherapy control apparatus 1 according to the present embodiment is implemented by a computer such as a personal computer, and mainly includes storage means 2 and computational processing means 3 as shown in FIG. 2, where the storage means 2 stores the radiotherapy control program 1a according to the present embodiment, various data, and the like, where the computational processing means 3 acquires and computationally processes various data.

The storage means 2 is made up of a ROM (Read Only Memory), a RAM (Random Access Memory), a HDD (Hard Disk Drive), a flash memory, and the like and configured to store various data and function as a working area when the computational processing means 3 performs computational processing. According to the present embodiment, the storage means 2 includes a program storage unit 21, a planned marker position storage unit 22, a template image storage unit 23 and a transformation matrix storage unit 24 as shown in FIG. 2. The individual components will be described below in more detail.

The radiotherapy control program 1a according to the present embodiment has been installed in the program storage unit 21. When the radiotherapy control program 1a is executed by the computational processing means 3, a computer is caused to function as individual components described later. Note that the use form of the radiotherapy control program 1a is not limited to the configuration described above. For example, the radiotherapy control program 1a may be stored in a computer-readable recording medium such as a CD-ROM or DVD-ROM, or the like and may be executed by being directly read out of the recording medium. Alternatively, the radiotherapy control program 1a stored on an external server or the like may be used via an ASP (Application Service Provider) systems or cloud computing systems.

The planned marker position storage unit 22 is designed to store planned positions, which are three-dimensional positions of markers at the time of treatment planning. According to the present embodiment, the planned marker position storage unit 22 is designed to store the planned positions acquired from the treatment planning device 11 by the planned marker position acquisition unit 31 (described later), by associating with the patient subjected to radiotherapy.

The template image storage unit 23 is designed to store template images used to identify projected positions of the markers on fluoroscopic images. The template image serves as a template when similarity and a predetermined region in a fluoroscopic image are calculated in a template pattern matching process described later. Specifically, the template image storage unit 23 stores in advance images of the markers implanted in the body of the patient, as template images. Note that when a marker to be used has a shape other than spherical, plural images obtained by taking pictures of the marker from various angles may be stored as template images.

The transformation matrix storage unit 24 is designed to store transformation matrices used to calculate equations of projection lines linking together the projected positions of markers on a fluoroscopic image and a focus position of the fluoroscopic imaging device 12. According to the present embodiment, a calibration operation is performed beforehand for the fluoroscopic imaging device 12 in each of the first fluoroscopic direction and second fluoroscopic direction. Then, two transformation matrices obtained by the calibration operations in the respective fluoroscopic directions are stored in the transformation matrix storage unit 24.

Next, the computational processing means 3, which is made up of a CPU (Central Processing Unit) and the like, is designed to execute the radiotherapy control program 1a installed in the storage means 2 and thereby implement a computer as the radiotherapy control apparatus 1 according to the present embodiment.

Specifically, as shown in FIG. 2, the radiotherapy control program 1a executed by the computational processing means 3 causes the computer to function as the planned marker position acquisition unit 31, a first fluoroscopic image acquisition unit 32, a fluoroscopic direction changing unit 33, a second fluoroscopic image acquisition unit 34, a first time-series data acquisition unit 35, a second time-series data acquisition unit 36, a correlation maximizing unit 37, a projection line calculation unit 38, an estimated marker position calculation unit 39, a patient aligning unit 40, a fluoroscopic image acquisition unit 41, an inter-marker distance acquisition unit 42, a marker position calculation unit 43, and a therapeutic radiation emission determination unit 44. The individual components will be described in more detail below.

The planned marker position acquisition unit 31 is designed to acquire planned positions, which are three-dimensional positions of markers at the time of treatment planning. According to the present embodiment, the planned marker position acquisition unit 31 acquires the planned positions of markers implanted in the patient to be subjected to radiotherapy from the treatment planning data storage unit 11a of the treatment planning device 11. Then, the planned positions are stored in the planned marker position storage unit 22.

The first fluoroscopic image acquisition unit 32 is designed to acquire plural first fluoroscopic images in the first fluoroscopic direction in a preparatory step before starting radiotherapy. According to the present embodiment, the first fluoroscopic image acquisition unit 32 outputs a radiography trigger to the X-ray generator 12a at predetermined time intervals and simultaneously outputs a synchronizing signal to the X-ray detector 12b. Consequently, plural first fluoroscopic images are acquired from the single fluoroscopic imaging device 12 set up in the first fluoroscopic direction in which the markers implanted in the body of the patient can be observed fluoroscopically.

The fluoroscopic direction changing unit 33 is designed to change the fluoroscopic direction of the fluoroscopic imaging device 12. Specifically, the fluoroscopic direction changing unit 33 outputs a drive command signal to the fluoroscopic direction drive device 13, and sets the X-ray generator 12a and the X-ray detector 12b to any desired positions and angles within a range in which the markers implanted in the body of the patient can be observed fluoroscopically. According to the present embodiment, the fluoroscopic direction changing unit 33 is designed to change the direction of the X-ray generator 12a and the X-ray detector 12b to at least a first fluoroscopic direction and a second fluoroscopic direction different from the first fluoroscopic direction. Note that preferably the angle formed by the first fluoroscopic direction and second fluoroscopic direction are close to 90 degrees.

The second fluoroscopic image acquisition unit 34 is designed to acquire plural second fluoroscopic images in the second fluoroscopic direction in a preparatory step before starting radiotherapy. According to the present embodiment, as in the case of the first fluoroscopic image acquisition unit 32, with the single fluoroscopic imaging device 12 set up in the second fluoroscopic direction by the fluoroscopic direction changing unit 33, the second fluoroscopic image acquisition unit 34 outputs a radiography trigger to the X-ray generator 12a at predetermined time intervals and outputs a synchronizing signal to the X-ray detector 12b. Consequently, plural second fluoroscopic images are acquired along the second fluoroscopic direction different from the first fluoroscopic direction with second acquisition timing different from acquisition timing of the first fluoroscopic images.

Note that although in the present embodiment, the first fluoroscopic image acquisition unit 32 and second fluoroscopic image acquisition unit 34 acquire fluoroscopic images directly from the fluoroscopic imaging device 12, the present invention is not limited to this configuration and fluoroscopic images taken by the fluoroscopic imaging device 12 may be acquired through the intervention of other devices. Also, although in the present embodiment, the first fluoroscopic image acquisition unit 32 and second fluoroscopic image acquisition unit 34 acquire fluoroscopic images in the form of plural still images, a video may be acquired alternatively.

The first time-series data acquisition unit 35 is designed to acquire time-sequential projected position of every marker on all the plural first fluoroscopic images as first time-series data. According to the present embodiment, the first time-series data acquisition unit 35 reads a template image out of the template image storage unit 23, and identifies the projected position of each marker on each first fluoroscopic image through a template pattern matching process based on normalized cross correlation. Then, when this process is performed for all the first fluoroscopic images, the first time-series data is acquired.

The second time-series data acquisition unit 36 is designed to acquire time-sequential projected position of every marker on all the plural second fluoroscopic images as second time-series data. According to the present embodiment, the second time-series data acquisition unit 36 identifies the projected position of each marker on each second fluoroscopic image through a process similar to that of the first time-series data acquisition unit 35. Then, when this process is performed for all the second fluoroscopic images, the second time-series data is acquired.

Note that although in the present embodiment, the first time-series data acquisition unit 35 and second time-series data acquisition unit 36 identify the projected positions of the markers through a template pattern matching process based on normalized cross correlation, the present invention is not limited to this processing method, and the projected positions may be identified based on mutual information or another image recognition technique may be adopted.

The correlation maximizing unit 37 is designed to maximize a correlation between the first time-series data and second time-series data. According to the present embodiment, estimated positions of the markers are calculated based on the first time-series data and second time-series data obtained with different timings as described later. However, when the first time-series data and second time-series data are periodic, calculation errors will increase if there is a phase difference between the two sets of data. Thus, according to the present embodiment to minimize the errors and thereby maximize the correlation between the first time-series data and second time-series data, the correlation maximizing unit 37 shifts the phase of the first time-series data or second time-series data.

The term "maximize the correlation" according to the present invention will be described below. In order to calculate a three-dimensional position of a marker, whereas fluoroscopic images taken simultaneously along two directions by two X-ray fluoroscopes and the like are used conventionally, the present embodiment uses the first time-series data and second time-series data obtained along two directions with different timings using the single fluoroscopic imaging device 12. Thus, the act of shifting the phase of the first time-series data or second time-series data and thereby establishing a correlation best suited to regard the two sets of data as having been obtained simultaneously will be referred to as "maximizing the correlation". As the correlation is maximized, the calculation errors in marker positions are minimized.

In describing the method for "maximizing the correlation" according to the present embodiment, first a technique for calculating a three-dimensional position of a marker based on fluoroscopic images taken along two directions will be described below. The technique is made up of four processes (1) to (4) below.

(1) Perform a calibration operation in each of the different fluoroscopic directions for the fluoroscopic imaging device 12 and find two transformation matrices in respective fluoroscopic directions beforehand.

Figure 3:
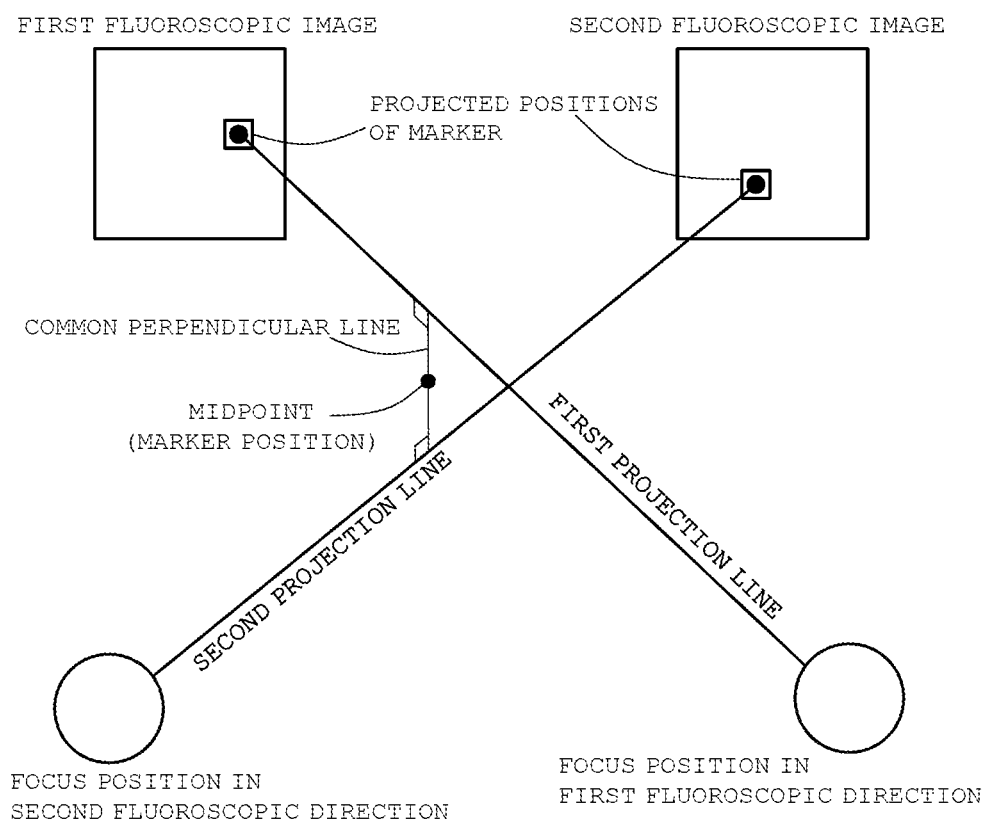
FIG. 3 is a diagram showing an example of a method for calculating a three-dimensional position of a marker from fluoroscopic images taken along two directions.

(2) Calculate the projected position of each marker in each of the two fluoroscopic images obtained along the different fluoroscopic directions, as shown in FIG. 3.

(3) Calculate equations of projection lines linking together the respective focus positions of the fluoroscopic imaging device 12 and the projected positions along the respective fluoroscopic directions based on the respective transformation matrices.

(4) The intersection between the calculated projection lines corresponds to the three-dimensional position of the marker.

However, when the projection lines do not intersect each other in process (4) above, a midpoint of a common perpendicular line which commonly intersects the projection lines at right angles is estimated to be the three-dimensional position of the marker as shown in FIG. 3. The shorter the common perpendicular line, the smaller the computational error in the estimated position, and the longer the common perpendicular line, the larger the computational error.

Thus, using the common perpendicular line as an index of the computational error, the correlation maximizing unit 37 according to the present embodiment is designed to shift the phase of the first time-series data or second time-series data so as to minimize the computational error, i.e., so as to minimize the length of the common perpendicular line.

Specifically, the correlation maximizing unit 37 first acquires equations of respective first projection lines linking the projected positions of the first time-series data with the focus position of the fluoroscopic imaging device 12 and respective equations of second projection lines linking the projected positions of the second time-series data with the focus position of the fluoroscopic imaging device 12 from the projection line calculation unit 38 described later and calculate the lengths of respective common perpendicular lines to the first projection lines and second projection lines.

Figure 4A:
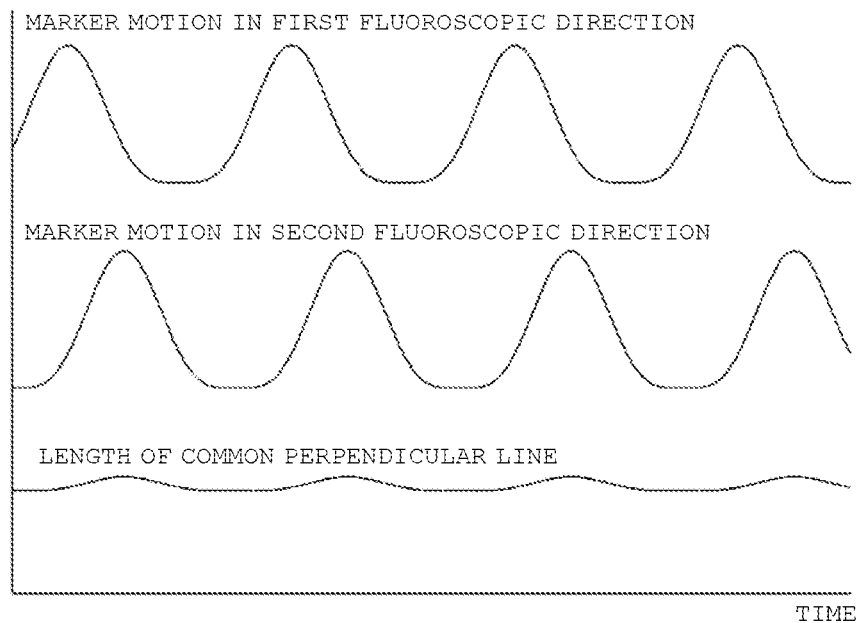
FIG. 4A is a graph showing length of a common perpendicular line in case which first time-series data and second time-series data differ in phase.
Figure 4B:
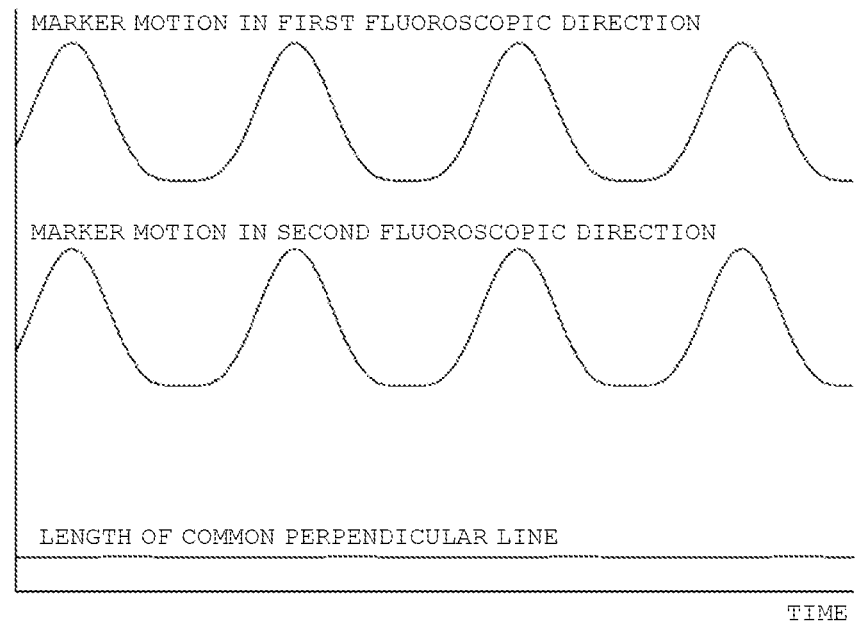
FIG. 4B is a graph showing length of a common perpendicular line in case which a correlation between the first time-series data and second time-series data is maximized.

As shown in FIG. 4A, the length of the common perpendicular line increases when there is a phase difference between the first time-series data and second time-series data. Thus, the correlation maximizing unit 37 calculates the length of the common perpendicular line sequentially while shifting the phase of the second time-series data little by little, and thereby searches for an amount of phase shift which will minimize the length of the common perpendicular line. Then, when the phase of the second time-series data is shifted by the amount of phase shift, the length of the common perpendicular line is minimized as shown in FIG. 4B, and so the computational error is minimized.

Note that although in the present embodiment, the correlation maximizing unit 37 finds the amount of phase shift which will minimize the length of the common perpendicular line, the present invention is not limited to this method. For example, the correlation maximizing unit 37 may determine the amount of phase shift such that inflection points in periodic movements of the first time-series data and second time-series data will coincide with each other. The inflection point in a periodic movement is, for example, the time at which a direction of motion is reversed by a change between exhalation and inhalation. Also, the correlation maximizing unit 37 may determine the amount of phase shift based on a correlation between time-sequential projected positions of each marker on fluoroscopic images obtained along different directions.

Also, when the minimized length of the common perpendicular line exceeds a predetermined threshold, the correlation maximizing unit 37 may notify the operator that the calculation error in the marker position is not permissible.

The projection line calculation unit 38 is designed to calculate equations of respective projection lines linking together the projected positions of the respective markers on the fluoroscopic image and a focus position of the fluoroscopic imaging device 12. Specifically, in a radiotherapy preparation step described later, the projection line calculation unit 38 acquires transformation matrices in the respective fluoroscopic directions from the transformation matrix storage unit 24 and then using the transformation matrices, the projection line calculation unit 38 calculates a coordinate group (linear equation) at which corresponding points of the projected positions making up the first time-series data and second time-series data in three-dimensional space can exist.

Specifically, if ML and MR denote transformation matrices in respective fluoroscopic directions, if <p1, p2, p3> denotes a coordinate point (x, y, z) of the marker in a three-dimensional space, if <pl1, pl2> and <pr1, pr2> denote points (x, y) of the marker on a two-dimensional fluoroscopic image, and if hl and hr are real numbers, the following relationship holds between three-dimensional space coordinates and two-dimensional coordinates.

<p1, p2, p3, 1>ML=hl<pl1, pl2, 1>
<p1, p2, p3, 1>MR=hr<pr1, pr2, 1>

When six expressions obtained by expanding the two expressions are solved for p1, p2, p3 using Gauss' theorem, equations of two projection lines corresponding to the first projection line and second projection line are found as shown below.

$$\begin{bmatrix} p1 \\ p2 \\ p3 \end{bmatrix} = \begin{bmatrix} al_1 \\ al_2 \\ al_3 \end{bmatrix} hl + \begin{bmatrix} bl_1 \\ bl_2 \\ bl_3 \end{bmatrix}$$

$$\begin{bmatrix} p1 \\ p2 \\ p3 \end{bmatrix} = \begin{bmatrix} ar_1 \\ ar_2 \\ ar_3 \end{bmatrix} hr + \begin{bmatrix} br_1 \\ br_2 \\ br_3 \end{bmatrix}$$

where $al_1$ to $al_3$, $ar_1$ to $ar_3$, $bl_1$ to $bl_3$, and $br_1$ to $br_3$ are all variables determined by Gauss' theorem.

On the other hand, in a radiotherapy step described later, using a template pattern matching process or the like, first the projection line calculation unit 38 identifies the projected positions of respective markers on the fluoroscopic image acquired by the fluoroscopic image acquisition unit 41. Then, the projection line calculation unit 38 acquires the transformation matrix in a fluoroscopic direction from the transformation matrix storage unit 24 and calculates equations of respective projection lines linking together the respective projected positions with the focus position of the fluoroscopic imaging device 12, using the transformation matrix.

Note that the fluoroscopic direction in a radiotherapy step may be the same as or different from the first fluoroscopic direction or second fluoroscopic direction in the radiotherapy preparation step. However, in the latter case, it is necessary to perform a calibration operation for the fluoroscopic imaging device 12 separately in the fluoroscopic direction for the radiotherapy step and store the transformation matrix in the fluoroscopic direction in the transformation matrix storage unit 24.

The estimated marker position calculation unit 39 is designed to calculate the estimated position of each marker in the preparatory step before starting radiotherapy. Specifically, in relation to the first time-series data and second time-series data after the correlation has been maximized by the correlation maximizing unit 37, the estimated marker position calculation unit 39 acquires equations of each first projection line and each second projection line from the projection line calculation unit 38 and calculates the midpoint of the common perpendicular line to each first projection line and each second projection line as the estimated position of the marker. Incidentally, since the estimated positions are obtained time-sequentially, not only relative position of the marker, but also three-dimensional motion of the marker is reorganized, and breathing exercise of the patient is kept track of as well.

The patient aligning unit 40 is designed to align the patient in a position suitable for emitting therapeutic radiation. According to the present embodiment, in conducting breathing synchronized radiotherapy, CT images taken in the expiratory phase are used during treatment planning. Therefore, the patient aligning unit 40 is designed to calculate positions in the expiratory phase based on the time-series data of the estimated positions calculated by the estimated marker position calculation unit 39, calculate a position correction amount of the patient bed 14*a* on which the patient is placed, such that the estimated positions of the markers in the expiratory phase will match the planned positions of the markers in the expiratory phase during the treatment planning. Then, the patient aligning unit 40 output the position correction amount as a position correction signal to the patient bed drive device 14.

Note that if a treatment plan is created based on CT images taken in the inspiratory phase, the patient aligning unit 40 can calculate positions in the inspiratory phase based on the time-series data of the estimated positions calculated by the estimated marker position calculation unit 39 and calculate a position correction amount of the patient bed 14*a* on which the patient is placed, such that the estimated positions of the markers in the inspiratory phase will match the planned positions of the markers in the inspiratory phase during the treatment planning.

The fluoroscopic image acquisition unit 41 is designed to sequentially acquire fluoroscopic images of the markers implanted in the body of the patient while radiotherapy is actually being conducted. According to the present embodiment, with the single fluoroscopic imaging device 12 set up in a predetermined fluoroscopic direction, the fluoroscopic image acquisition unit 41 outputs a radiography trigger to the X-ray generator 12a at predetermined time intervals and at the same time outputs a synchronizing signal to the X-ray detector 12b. Consequently, an image of three or more markers implanted in the body of the patient is acquired.

Figure 5:
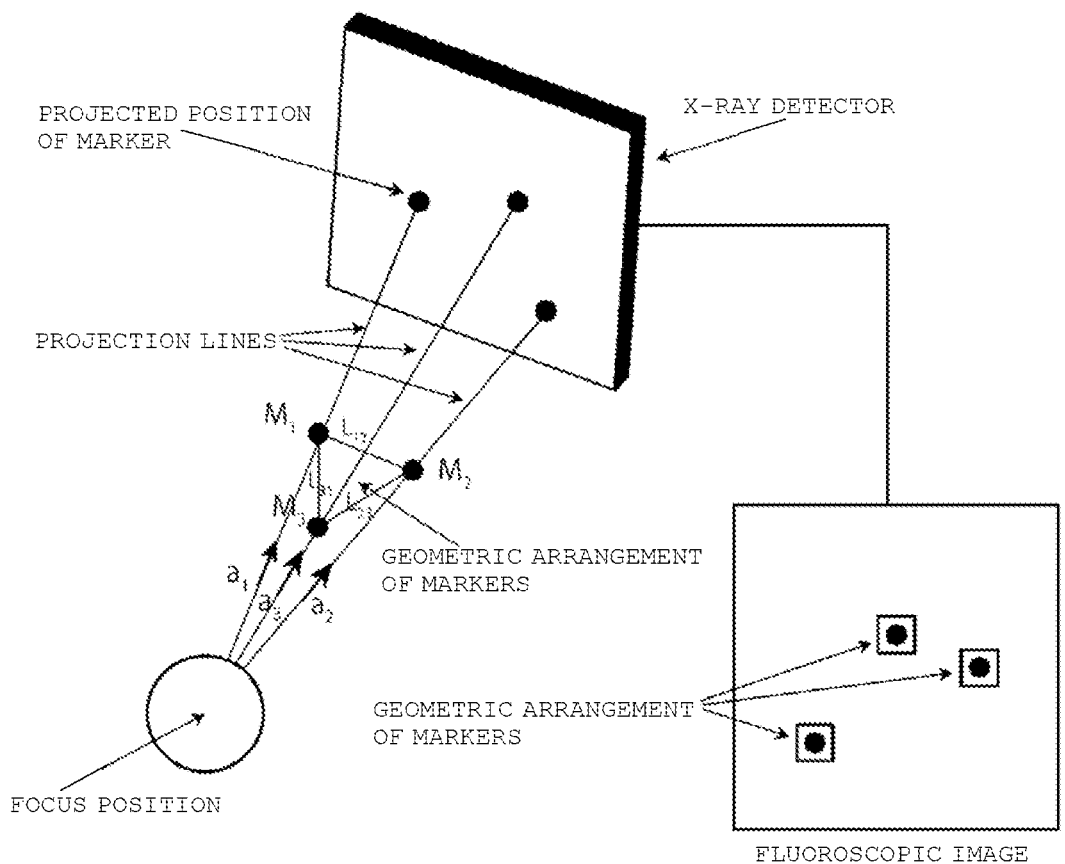
FIG. 5 is a diagram showing a method for calculating a three-dimensional position of a marker based on a fluoroscopic image taken along one direction, according to the present embodiment.

The inter-marker distance acquisition unit 42 is designed to acquire each distance between each pair of the markers. According to the present embodiment, the inter-marker distance acquisition unit 42 acquires the inter-marker distances based on estimated positions of the markers calculated by the estimated marker position calculation unit 39. Specifically, as shown in FIG. 5, when the estimated positions of three markers $M_1$, $M_2$, and $M_3$ are defined as three-dimensional vectors $\vec{M}_1$, $\vec{M}_2$, and $\vec{M}_3$, a distance $L_{12}$ between the markers $M_1$ and $M_2$, a distance $L_{23}$ between the markers $M_2$ and $M_3$, and a distance $L_{31}$ between the markers $M_3$ and $M_1$ are given by Formula (2) below.

$$|\vec{M}_1 - \vec{M}_2| = L_{12}$$

$$|\vec{M}_2 - \vec{M}_3| = L_{23}$$

$$|\vec{M}_3 - \vec{M}_1| = L_{31} \qquad \text{Formula (2)}$$

Note that although in the present embodiment, the inter-marker distance acquisition unit 42 acquires the inter-marker distances based on the estimated positions of the markers calculated by the estimated marker position calculation unit 39, the present invention is not limited to this configuration. For example, by identifying the relative positions of markers based on patient's CT images taken in advance, the inter-marker distances may be acquired based on the relative positions.

The marker position calculation unit 43 is designed to calculate the current position of each marker while radiotherapy is actually being conducted. According to the present embodiment, the marker position calculation unit 43 calculates the current positions of markers based on the equations of respective projection lines and on the inter-marker distances.

Specifically, as shown in FIG. 5, if the three-dimensional direction vectors of respective projection lines are $a_1$, $a_2$, and $a_3$ and the three-dimensional vector of the focus position of the fluoroscopic imaging device 12 is b, the three-dimensional vectors $M_1$, $M_2$, and $M_3$ as the current positions of markers in a treatment room coordinate space are defined by Formula (1) below. Thus, the marker position calculation unit 43 is designed to identify the three-dimensional vectors $M_1$, $M_2$, and $M_3$ by calculating $t_1$, $t_2$, and $t_3$ in Formula (1) below based on the three-dimensional vectors $a_1$, $a_2$, $a_3$, and b identified by the equations of respective projection lines calculated by the projection line calculation unit 38 and on the inter-marker distances acquired by the inter-marker distance acquisition unit 42.

$$\vec{M}_1 = t_1 \vec{a}_1 + \vec{b}$$

$$\vec{M}_2 = t_2 \vec{a}_2 + \vec{b}$$

$$\vec{M}_3 = t_3 \vec{a}_3 + \vec{b} \qquad \text{Formula (1)}$$

Note that even if four or more markers are implanted in the body of the patient, the current positions of the markers may be calculated by solving equations similar to Formula (1) above. Alternatively, the current positions may be calculated by selecting any three markers from four or more markers.

The therapeutic radiation emission determination unit 44 is designed to determine whether to emit therapeutic radiation, based on the current position of each marker. Specifically, the therapeutic radiation emission determination unit 44 compares the current position of the marker calculated by the marker position calculation unit 43 with the planned position of the marker acquired by the marker planned position acquisition unit 31. Then, when the current position falls within a predetermined tolerance of the planned position, the therapeutic radiation emission determination unit 44 determines that therapeutic radiation is to be emitted. On the other hand, when the current position falls outside the predetermined tolerance of the planned position, the therapeutic radiation emission determination unit 44 determines that therapeutic radiation is not to be emitted. Based on the determination results, the enable-emission gate signal of the therapeutic radiation gate control device 15 is designed to be set to on or off.

Next, description will be given of operation of the radiotherapy control apparatus 1, radiotherapy system 10 which includes the radiotherapy control apparatus 1, and radiotherapy method driven by the radiotherapy control program 1a according to the present embodiment.

Figure 6:
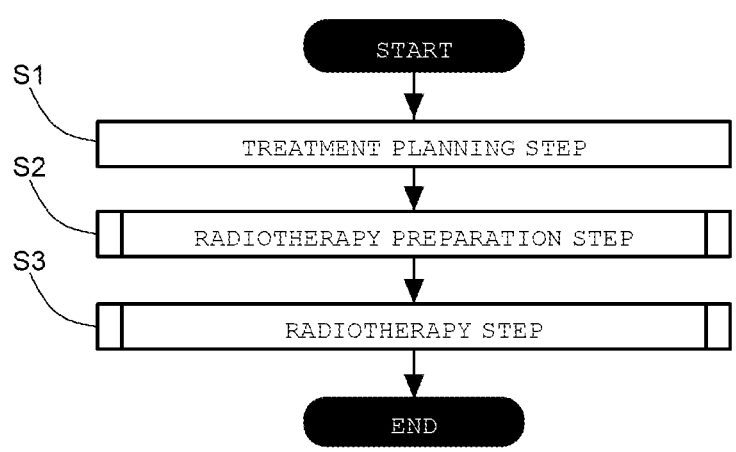
FIG. 6 is a flowchart showing steps of radiotherapy carried out by a radiotherapy control program and the radiotherapy system according to the present embodiment.

As shown in FIG. 6, the radiotherapy method performed in the present embodiment is roughly divided into a treatment planning step (step S1) of creating a treatment plan, a radiotherapy preparation step (step S2) of preparing data necessary for radiotherapy and setting up the patient, and a radiotherapy step (step S3) of conducting radiotherapy by actually irradiating an affected area of the patient with therapeutic radiation.

First, a treatment planning step involves creating a treatment plan beforehand for the patient to be subjected to radiotherapy (step S1). Specifically, based on the patient's CT images acquired using a predetermined CT system, the treatment planning device 11 calculates treatment planning data including, planned marker positions, an irradiation sequence (irradiation doses, irradiation postures), prescribed doses, a radiation dose distribution, and the like and stores the data in the treatment planning data storage unit 11a beforehand.

Figure 7:
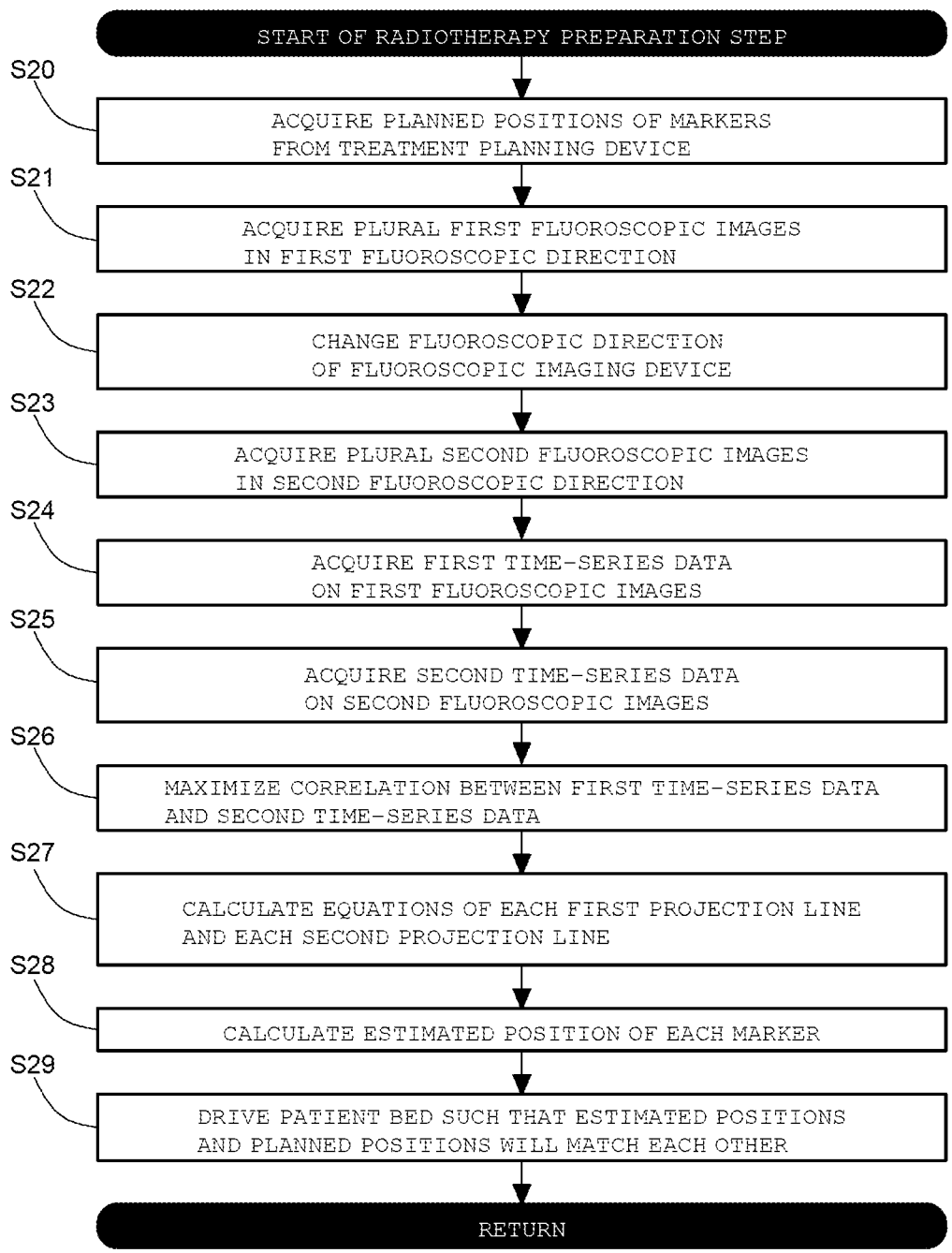
FIG. 7 is a flowchart showing operation of a radiotherapy preparation step carried out by the radiotherapy control program and radiotherapy system according to the present embodiment.

Next, the radiotherapy preparation step involves making various preparations just before starting radiotherapy (step S2). Specifically, as shown in FIG. 7, first the planned marker position acquisition unit 31 acquires planned positions of markers from the treatment planning data storage unit 11a of the treatment planning device 11 and stores the planned positions in the planned marker position storage unit 22 (step S20). Consequently, a region within a predetermined tolerance is set from each planned position as a region to which therapeutic radiation is to be emitted by waiting for a marker.

Note that in step S20, the treatment planning device 11 separately transmits data such as the irradiation sequence (irradiation doses, irradiation postures), prescribed doses, and radiation dose distribution stored in the treatment planning data storage unit 11a to the radiation control and monitoring device 16.

Next, the first fluoroscopic image acquisition unit 32 acquires plural first fluoroscopic images from the single fluoroscopic imaging device 12 set up in the first fluoroscopic direction (step S21), and then the fluoroscopic direction changing unit 33 changes the fluoroscopic direction of fluoroscopic imaging device 12 to the second fluoroscopic direction by controlling the fluoroscopic direction drive device 13 (step S22). Then, the second fluoroscopic image acquisition unit 34 acquires plural second fluoroscopic images in the second fluoroscopic direction (step S23). Consequently, fluoroscopic images taken along two different fluoroscopic directions with different timings are obtained using only one fluoroscopic imaging device 12.

Next, the first time-series data acquisition unit 35 identifies the projected position of each marker on each first fluoroscopic image and thereby acquires first time-series data (step S24) and the second time-series data acquisition unit 36 identifies the projected position of each marker on each second fluoroscopic image and thereby acquires second time-series data (step S25). Then, the correlation between the first time-series data and second time-series data is maximized by the correlation maximizing unit 37 (step S26).

In so doing, according to the present embodiment, the correlation maximizing unit 37 shifts the phase of the first time-series data or second time-series data so as to minimize the length of the common perpendicular line to the first projection line and second projection line. This eliminates the phase difference between the first time-series data and second time-series data, producing data which can be regarded to be equivalent to data obtained simultaneously along two directions using two fluoroscopic imaging devices 12 and thereby minimizing calculation errors in the estimated positions of the markers.

Next, the projection line calculation unit 38 calculates equations of each first projection line and each second projection line with the correlation between the first time-series data and second time-series data maximized in step S26 (step S27) and the midpoint of the common perpendicular line to each first projection line and each second projection line is calculated as the estimated position of a marker by the estimated marker position calculation unit 39 (step S28). The above process reorganizes the three-dimensional motion of each marker based on fluoroscopic images obtained along different directions at different times using the single fluoroscopic imaging device 12. This makes it possible to keep track of positional relationships which represent a geometric arrangement of plural markers as well as breathing exercise of the patient.

Next, the patient aligning unit 40 controls the patient bed drive device 14 and drives the patient bed 14a such that the estimated positions calculated in step S28 and the planned positions acquired in step S20 will match each other (step S29). Consequently, the three-dimensional positions, in the treatment room coordinate space, of the markers implanted in the patient are brought into coincidence with the planned positions established during the treatment planning getting ready to conduct breathing synchronized radiotherapy.

Note that if CT images of the patient are taken separately just before the start of the radiotherapy step described in detail below (step S3) and the marker positions obtained from the CT images fall within a predetermined tolerance of the planned positions, steps S21 to S29 described above may be omitted.

Figure 8:
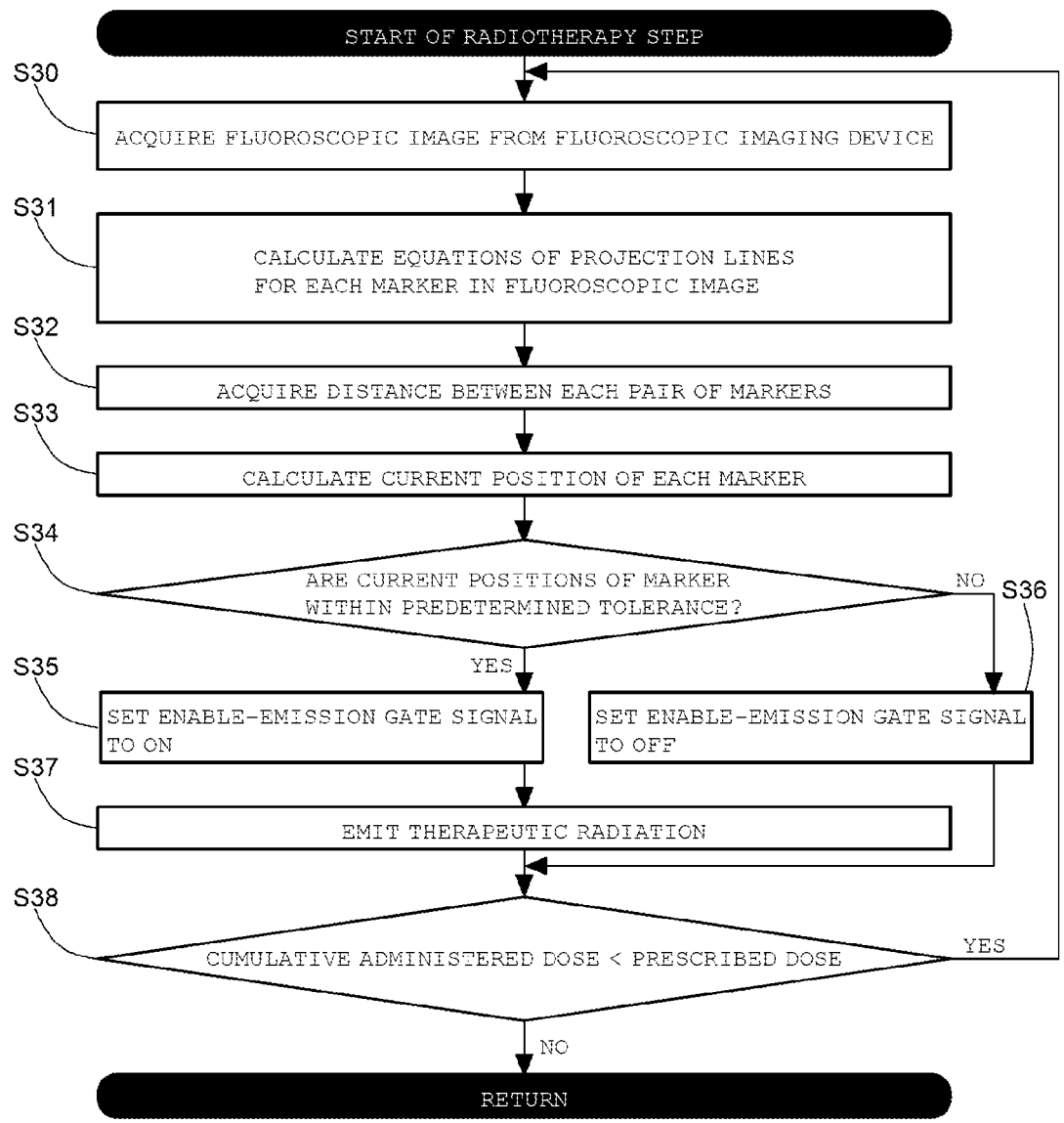
FIG. 8 is a flowchart showing operation of a radiotherapy step carried out by the radiotherapy control program and radiotherapy system according to the present embodiment.

The radiotherapy step involves conducting radiotherapy by actually irradiating an affected area of the patient with therapeutic radiation (step S3). Specifically, as shown in FIG. 8, first the fluoroscopic image acquisition unit 41 acquires a fluoroscopic image from the single fluoroscopic imaging device 12 (step S30), and then the projection line calculation unit 38 identifies the projected positions of the markers contained in the fluoroscopic image and calculates equations of respective projection lines linking together the respective projected positions with the focus position of the fluoroscopic imaging device 12 (step S31).

Next, based on the estimated positions of the markers calculated in step S28, the inter-marker distance acquisition unit 42 acquires inter-marker distances (step S32), and then the marker position calculation unit 43 calculates the current positions of the markers based on the equations of the projection lines calculated in step S31 and the inter-marker distances acquired in step S32 (step S33).

Consequently, whereas fluoroscopic images taken simultaneously along two directions using two fluoroscopic imaging devices 12 are needed conventionally in order to calculate the current positions of markers during radiotherapy, the present embodiment can calculate the current positions only using a fluoroscopic image taken along one direction by the single fluoroscopic imaging device 12. Thus, by simple arithmetic, a radiation exposure dose inflicted on the patient by radiographic radiation for fluoroscopic observation during radiotherapy is halved compared to conventional radiotherapy.

Next, the therapeutic radiation emission determination unit 44 compares the planned marker positions acquired in step S20 with the current marker positions calculated in step S33 (step S34). Then, when the current positions fall within a predetermined tolerance of the planned positions (YES in step S34), the therapeutic radiation emission determination unit 44 determines that therapeutic radiation is to be emitted and sets the enable-emission gate signal of the therapeutic radiation gate control device 15 to on (step S35).

While the enable-emission gate signal of the therapeutic radiation gate control device 15 remains on, the radiation control and monitoring device 16 outputs an emission command signal to the therapeutic radiation emission device 17 according to the irradiation sequence acquired in step S20, causing therapeutic radiation is to be emitted (step S37). On the other hand, when the current positions fall outside the predetermined tolerance of the planned positions (NO in step S34), the therapeutic radiation emission determination unit 44 determines that therapeutic radiation is not to be emitted and sets the enable-emission gate signal of the therapeutic radiation gate control device 15 to off (step S36).

In this way, by waiting for the markers to fall within a predetermined tolerance, therapeutic radiation is emitted only when the markers are within the predetermined tolerance. This improves irradiation accuracy with respect to affected areas and reduces mis-irradiation with respect to normal areas.

Finally, the radiation control and monitoring device 16 compares the cumulative administered dose administered to the patient with the prescribed dose acquired in step S20 (step S38). Then, unless the cumulative administered dose does not reach the prescribed dose (YES in step S38), the flow returns to step S30 to continue radiotherapy. On the other hand, when the cumulative administered dose reaches the prescribed dose (NO in step S38), the radiotherapy is finished.

The radiotherapy control apparatus 1 and radiotherapy control program 1a according to the present embodiment described above provide the following operational advantages.

1. The current positions of markers can be calculated from fluoroscopic images obtained using a single fluoroscopic imaging device 12.
2. A radiation exposure dose inflicted on the patient by radiographic radiation during radiotherapy can be reduced.
3. The estimated positions of markers can be calculated on based fluoroscopic images obtained along different fluoroscopic directions with different timings using the single fluoroscopic imaging device 12.

4. Calculation errors in the estimated positions of the markers can be reduced by shifting the phase so as to maximize the correlation between the first time-series data and the second time-series data.

5. Therapeutic radiation is emitted only when the markers are within the predetermined tolerance, making it possible to improve irradiation accuracy with respect to affected areas and reduce mis-irradiation with respect to normal areas.

Note that the radiotherapy control apparatus 1 and radiotherapy control program 1a according to the present invention are not limited to the embodiment described above, and can be changed as appropriate.

For example, although the radiotherapy system 10 according to the present embodiment described above is equipped with only one fluoroscopic imaging device 12, the present invention is not limited to this configuration. For example, even when the radiotherapy system 10 is equipped with two fluoroscopic imaging devices 12, if the radiotherapy control apparatus 1 and radiotherapy control program 1a according to the present invention are applied and if only one fluoroscopic imaging device 12 is used in the radiotherapy step, the operational advantages of the present invention can be available. Note that in this case, in calculating estimated positions in the radiotherapy preparation step, the radiotherapy system 10 may be used plural fluoroscopic images taken simultaneously along different directions using two fluoroscopic imaging devices 12. This makes it possible to apply the present invention even to a conventional system which uses two fluoroscopic imaging devices 12 and thereby reduce the burden of investment. Then, if one or two fluoroscopic imaging devices 12 are used selectively as appropriate according to conditions of the patient, radiotherapy can be carried on with less burden on the patient.

Also, although in the present embodiment described above, the current positions of markers are calculated by assuming that the distance between markers is constant, the present invention is not limited to this configuration. Actually, the distance between markers varies slightly with the breathing of the patient, and thus calculation accuracy of the current positions can be improved if this variation is taken into consideration.

Furthermore, although in the present embodiment described above, fluoroscopic images are acquired using X-rays fluoroscopic images may be acquired by another fluoroscopic image acquisition method such as using ultrasound other than X-rays. Also, although in the present embodiment, X-rays are used as therapeutic radiation, a proton beam, heavy-particle beam, or the like other than X-rays may be used.

REFERENCE SIGNS LIST

1 Radiotherapy control apparatus
1a Radiotherapy control program
2 Storage means
3 Computational processing means
10 Radiotherapy system
11 Treatment planning device
11a Treatment planning data storage unit
12 Fluoroscopic imaging device
12a X-ray generator
12b X-ray detector
13 Fluoroscopic direction drive device
14 Patient bed drive device
14a Patient bed
15 Therapeutic radiation gate control device
16 Radiation control and monitoring device
17 Therapeutic radiation emission device
21 Program storage unit
22 Planned marker position storage unit
23 Template image storage unit
24 Transformation matrix storage unit
31 Planned marker position acquisition unit
32 First fluoroscopic image acquisition unit
33 Fluoroscopic direction changing unit
34 Second fluoroscopic image acquisition unit
35 First time-series data acquisition unit
36 Second time-series data acquisition unit
37 Correlation maximizing unit
38 Projection line calculation unit
39 Estimated marker position calculation unit
40 Patient aligning unit
41 Fluoroscopic image acquisition unit
42 Inter-marker distance acquisition unit
43 Marker position calculation unit
44 Therapeutic radiation emission determination unit

The invention claimed is:

1. A radiotherapy control apparatus, comprising:
a single fluoroscopic imaging device adapted to emit radiographic radiation;
a fluoroscopic image acquisition unit adapted to acquire a fluoroscopic image of three or more markers implanted in the body of a patient, the fluoroscopic image being a single image that is taken by the radiographic radiation, which is emitted from the single fluoroscopic imaging device while the patient is in a radiotherapy, and in a single view of the fluoroscopic image acquisition unit;
a projection line calculation unit adapted to identify projected positions of the respective markers on the fluoroscopic image and calculate equations of respective projection lines linking together these projected positions and a focus position of the fluoroscopic imaging device;
an inter-marker distance acquisition unit adapted to acquire inter-maker distances between each pair of the markers;
a marker position calculation unit adapted to calculate current positions of the respective markers based on the equations of the projection lines and the inter-marker distances; and
a therapeutic radiation emission determination unit adapted to determine whether to emit therapeutic radiation based on the current positions of the respective markers.

2. The radiotherapy control apparatus according to claim 1, wherein when three-dimensional vectors $M_1$, $M_2$, and $M_3$ which represent the current positions of the respective markers are defined by Formula (1) below using three-dimensional direction vectors $a_1$, $a_2$, and $a_3$ of the respective projection lines and a three-dimensional vector b of the focus position, the marker position calculation unit identifies the three-dimensional vectors $M_1$, $M_2$, and $M_3$ by calculating coefficients $t_1$, $t_2$, and $t_3$ in Formula (1) below based on the three-dimensional vectors $a_1$, $a_2$, $a_3$, and b identified by the equations of the respective projection lines as well as on the inter-marker distances $$\vec{M}_1 = t_1 \vec{a}_1 + \vec{b}$$

$$\vec{M}_2 = t_2 \vec{a}_2 + \vec{b}$$

$$\vec{M}_3 = t_3 \vec{a}_3 + \vec{b} \qquad \text{Formula (1)}.$$

3. The radiotherapy control apparatus according to claim 1, further comprising:
a first fluoroscopic image acquisition unit adapted to acquire a plurality of first fluoroscopic images taken by the single fluoroscopic imaging device along a first fluoroscopic direction;
a second fluoroscopic image acquisition unit adapted to acquire a plurality of second fluoroscopic images taken by the single fluoroscopic imaging device along a second fluoroscopic direction different from the first fluoroscopic direction with second acquisition timing different from acquisition timing of the first fluoroscopic images;
a first time-series data acquisition unit adapted to acquire time-sequential projected positions of the markers in the plurality of first fluoroscopic images as first time-series data;
a second time-series data acquisition unit adapted to acquire time-sequential projected positions of the markers in the plurality of second fluoroscopic images as second time-series data;
a correlation maximizing unit adapted to maximize a correlation between the first time-series data and the second time-series data by shifting a phase of the first time-series data or the second time-series data; and
an estimated marker position calculation unit adapted to acquire equations of respective first projection lines linking the projected positions of the first time-series data with the focus position and equations of respective second projection lines linking the projected positions of the second time-series data with the focus position from the projection line calculation unit after the correlation is maximized by the correlation maximizing unit and calculate midpoints of respective common perpendicular lines to the first projection lines and the second projection lines as estimated positions of the markers, wherein
the inter-marker distance acquisition unit acquires the inter-marker distances based on estimated positions of the markers calculated by the estimated marker position calculation unit.

4. The radiotherapy control apparatus according to claim 3, wherein the correlation maximizing unit shifts a phase of the first time-series data or the second time-series data so as to minimize lengths of the common perpendicular lines to the first projection lines and the second projection lines.

5. The radiotherapy control apparatus according to claim 1, further comprising a planned marker position acquisition unit adapted to acquire planned positions from a treatment planning data storage unit adapted to store data on treatment planning, the planned positions being three-dimensional positions of the markers at a time of the treatment planning, wherein
the therapeutic radiation emission determination unit compares the current position of each of the markers calculated by the marker position calculation unit with the planned position of the marker acquired by the planned marker position acquisition unit and thereby determines whether or not the current position falls within a predetermined tolerance of the planned position.

6. A non-transitory computer-readable computer medium storing a radiotherapy control program configured to cause a computer to function as:
a fluoroscopic image acquisition unit adapted to acquire a fluoroscopic image of three or more markers implanted in the body of a patient from a single fluoroscopic imaging device adapted to emit radiographic radiation, the fluoroscopic image being a single image that is taken by the radiographic radiation, which is emitted from the single fluoroscopic imaging device while the patient is in a radiotherapy, and in a single view of the fluoroscopic image acquisition unit;
a projection line calculation unit adapted to identify projected positions of the respective markers on the fluoroscopic image and calculate equations of respective projection lines linking together these projected positions and a focus position of the fluoroscopic imaging device;
an inter-marker distance acquisition unit adapted to acquire inter-maker distances between each pair of the markers;
a marker position calculation unit adapted to calculate current positions of the respective markers based on the equations of the projection lines and the inter-marker distances; and
a therapeutic radiation emission determination unit adapted to determine whether to emit therapeutic radiation based on the current positions of the respective markers.

7. The non-transitory computer-readable computer medium storing the radiotherapy control program according to claim 6, wherein when three-dimensional vectors $M_1$, $M_2$, and $M_3$ which represent the current positions of the respective markers are defined as Formula (1) below using three-dimensional direction vectors $a_1$, $a_2$, and $a_3$ of the respective projection lines and a three-dimensional vector b of the focus position, the marker position calculation unit identifies the three-dimensional vectors $M_1$, $M_2$, and $M_3$ by calculating coefficients $t_1$, $t_2$, and $t_3$ in Formula (1) below based on the three-dimensional vectors $a_1$, $a_2$, $a_3$, and b identified by the equations of the respective projection lines as well as on the inter-marker distances $$\vec{M}_1 = t_1 \vec{a}_1 + \vec{b}$$

$$\vec{M}_2 = t_2 \vec{a}_2 + \vec{b}$$

$$\vec{M}_3 = t_3 \vec{a}_3 + \vec{b} \qquad \text{Formula (1).}$$

8. The non-transitory computer-readable computer medium storing the radiotherapy control program according to claim 6, further configured to cause the computer to function as:
a first fluoroscopic image acquisition unit adapted to acquire a plurality of first fluoroscopic images taken by the single fluoroscopic imaging device along a first fluoroscopic direction;
a second fluoroscopic image acquisition unit adapted to acquire a plurality of second fluoroscopic images taken by the single fluoroscopic imaging device along a second fluoroscopic direction different from the first fluoroscopic direction with second acquisition timing different from acquisition timing of the first fluoroscopic images;
a first time-series data acquisition unit adapted to acquire time-sequential projected positions of the markers in the plurality of first fluoroscopic images as first time-series data;

a second time-series data acquisition unit adapted to acquire time-sequential projected positions of the markers in the plurality of second fluoroscopic images as second time-series data;

a correlation maximizing unit adapted to maximize a correlation between the first time-series data and the second time-series data by shifting a phase of the first time-series data or the second time-series data; and an estimated marker position calculation unit adapted to acquire equations of respective first projection lines linking the projected positions of the first time-series data with the focus position and equations of respective second projection lines linking the projected positions of the second time-series data with the focus position from the projection line calculation unit after the correlation is maximized by the correlation maximizing unit and calculate midpoints of respective common perpendicular lines to the first projection lines and the second projection lines as estimated positions of the markers, wherein the inter-marker distance acquisition unit acquires the inter-marker distances based on estimated positions of the markers calculated by the estimated marker position calculation unit.

9. The non-transitory computer-readable computer medium storing the radiotherapy control program according to claim 8, wherein the correlation maximizing unit shifts a phase of the first time-series data or the second time-series data so as to minimize lengths of the common perpendicular lines to the first projection lines and the second projection lines.

10. The non-transitory computer-readable computer medium storing the radiotherapy control program according to claim 6, further configured to cause the computer to function as a planned marker position acquisition unit adapted to acquire planned positions from a treatment planning data storage unit adapted to store data on treatment planning, the planned positions being three-dimensional positions of the markers at a time of the treatment planning, wherein the therapeutic radiation emission determination unit compares the current position of each of the markers calculated by the marker position calculation unit with the planned position of the marker acquired by the planned marker position acquisition unit and thereby determines whether or not the current position falls within a predetermined tolerance of the planned position.

* * * * *